(12) United States Patent
Poche

(10) Patent No.: US 6,264,969 B1
(45) Date of Patent: Jul. 24, 2001

(54) MOLE CONTROL SYSTEM

(75) Inventor: Richard M. Poche, Wellington, CO (US)

(73) Assignee: Genesis Laboratories, Inc., Wellington, CO (US)

(*) Notice: Subject to any disclaimer, the term of this patent is extended or adjusted under 35 U.S.C. 154(b) by 0 days.

(21) Appl. No.: 09/277,897

(22) Filed: Mar. 29, 1999

(51) Int. Cl.⁷ .................................................. A01N 25/10
(52) U.S. Cl. ..................... 424/410; 424/405; 424/406; 424/407; 424/409; 424/417; 424/418; 424/419; 424/420; 424/442; 424/84; 424/641; 514/457; 514/460; 514/494; 514/681
(58) Field of Search ............ 43/124, 131; 424/405–407, 424/409, 410, 417–420, 442, 84, 641; 514/494, 460, 681, 457

(56) References Cited

U.S. PATENT DOCUMENTS

| 2,957,804 | * | 10/1960 | Shuyler | 167/46 |
| 4,520,015 | * | 5/1985 | Pesche | 424/153 |
| 4,748,185 | * | 5/1988 | Entwistle et al. | 514/457 |
| 4,829,706 | * | 5/1989 | Perry | 43/125 |
| 4,833,818 | * | 5/1989 | Berta | 43/124 |
| 4,841,668 | * | 6/1989 | McKenzie | 43/124 |
| 5,017,620 | * | 5/1991 | Grassman et al. | 514/693 |

OTHER PUBLICATIONS

Moles (Henderson) p. D53–61, 1983.*
Poche Proceedings, 13th Great Plains Wildlife Damage Control Workshop Mole Census Techniques pp. 114–116, 1997.*
Nowak: Insectivor Walker's Mammal's of the World pp. 167, 168, 1991.*

* cited by examiner

*Primary Examiner*—Neil S. Levy
(74) *Attorney, Agent, or Firm*—Dean P. Edmundson

(57) ABSTRACT

A method is described for controlling or exterminating moles through the use of a bait composition in the form of a gel, paste, or grease. The composition includes an attractant and an active ingredient capable of killing vertebrate pests. The composition is injected into a mole tunnel through a small diameter nozzle, tube or needle to avoid digging open the tunnel or causing it to collapse.

2 Claims, No Drawings

MOLE CONTROL SYSTEM

FIELD OF THE INVENTION

This invention relates to methods and systems for controlling various types of moles. More particularly, this invention relates to methods for controlling moles with a bait composition.

BACKGROUND OF THE INVENTION

Moles are subterranean animals that can cause considerable damage to lawns, golf courses, etc. by burrowing through the ground just beneath the surface. These animals are insectivores that subsist on earthworms, grubs, and insects which inhabit the ground. Moles create a system of shallow tunnels in the soil, normally about 2–3 inches below the surface, and the displaced soil creates a ridge in the ground surface.

Previous techniques for controlling moles have involved mechanical traps and poison baits. The mechanical traps may catch a mole occasionally, but they are labor intensive and not usually effective in totally eliminating moles. The use of poison baits (e.g., pellets) require that a person first dig open one of the tunnels, drop the bait into the tunnel, and then close the tunnel without covering the bait. The act of opening the tunnel, however, may cause the moles to avoid that particular tunnel in the future.

There has not heretofore been provided an effective and reliable method or system for controlling or exterminating moles in the ground.

SUMMARY OF THE INVENTION

In accordance with the present invention an effective method is provided for controlling moles without the use of mechanical traps and without having to dig out a tunnel.

In a preferred embodiment the method of the invention comprises injecting an amount of a gel, paste, or grease composition into a mole tunnel, with minimal disturbance of the soil, wherein the composition comprises an attractant and an active ingredient. Because the composition is in gel, paste, or grease form, it will not be absorbed into the soil. Rather, it remains in a clump and it is easily ingested by moles.

The method of the invention is effective for controlling various types of moles, e.g. the eastern mole (*Scalopus aquaticus*), Townsend mole (*Scapanus townsendi*), hairytail mole (*Parascalops breweri*), California mole (*Scapanus latimanus*) and the starnose mole (*Condylura cristata*).

By injecting the gel, paste, or grease composition into the tunnel with a small diameter nozzle, tube, or needle, there is minimal disturbance of the soil, and the tunnel is neither opened nor collapsed or caved in. Therefore, there is no danger of burying the bait composition with soil.

Other features and advantages of the method and system of the invention will be apparent from the following detailed description.

DETAILED DESCRIPTION OF THE INVENTION

In accordance with the present invention, a bait composition is prepared which is in the form of a gel, paste, or grease composition. It is a viscous composition, however, will not soak into the soil.

The bait composition comprises an attractant and an active ingredient (i.e., a poison). Preferred attractants include blood meal, bone meal, fish meal, or insect or worm parts. It is also possible to use pet food as an attractant. The active ingredient may be any suitable EPA-approved pesticide such as warfarin, chlorophacinone, diphacinone, bromadiolone, brodifacoum, bromethalin, zinc phosphide, etc.

The amount of active ingredient present in the composition may vary. Typically the amount present is about 50 to 500 ppm, although bromethalin should be at a concentration of about 0.01 to 0.1% if it is used, and if zinc phosphide is used it should be present in an amount of about 2% by weight.

The composition also preferably includes sugar (about 0.5%) to improve palatability. Various types of sweeteners may be used for this purpose.

The gelling agent in the composition is preferably water soluble and may be present in an amount from about 35 to 75% by weight. A variety of gelling agents are useful, e.g., methylcellulose, sorbitol, food gums, gelatin, non-petroleum greases that are biodegradable, etc.

The bait composition is preferably loaded into a cartridge, syringe, or other container with a small diameter dispensing nozzle (e.g., less than about 0.25 inch). The length of the nozzle is preferably about 3 to 4 inches long so that it can penetrate into the ground sufficiently deep to enable the bait composition to be injected into the mole tunnel. Preferably, from 0.25 to 1 ounce of composition is injected at each selected location. It is also preferred to inject the composition into the mole tunnels at several different locations. It is also possible to inject the composition into the tunnel using a needle or a small diameter tube. All of these are considered to be equivalent for the purposes of this invention.

A field study was conducted using a mole gel bait of the invention containing 0.05% by weight warfarin. The composition was injected into mole tunnels at the rate of 1 ounce every 50 feet in 10 eastern mole burrow systems. Five days after applying the bait, mole activity was reduced by 50%. Since warfarin generally requires 5–7 days to kill a mole, the projected efficacy of control was expected to be greater over time. Normally such an application requires 21 days of observation to attain final figures.

Other variants are also possible within this invention.

What is claimed is:

1. A method for controlling moles comprising the steps of:

(a) providing a container having a dispensing nozzle, tube or needle with a diameter less than about 0.25 inch;

(b) filling said container with a composition comprising an attractant and an active ingredient; the attractant being selected from the group consisting of blood meal, fish meal, earthworms, grubs and insect parts, the active ingredient being selected from the group consisting of 50 to 500 ppm of warfarin, chlorophacinone, diphacinone, bromodiolone, brodifacoum, 0.01% bromethaline, and 2% zinc phosphide, wherein said composition comprises about 35% to 75% by weight of a water-soluble gel material, paste or grease, (c) locating a mole tunnel in the ground;

(d) forcing said nozzle, tube, or needle into the ground to reach said tunnel;

(e) dispensing 0.25 to 1 ounce of said composition into said tunnel through said nozzle, tube or needle at each selected location; and (f) observing and identifying the level of mole activity after 5 days to determine whether the desired reduction in activity has been attained.

2. A method in accordance with claim 1, wherein said composition further comprises sweetener and non-petroleum grease.

* * * * *